United States Patent
Gazielly et al.

[11] Patent Number: 5,441,508
[45] Date of Patent: Aug. 15, 1995

[54] REINFORCEMENT AND SUPPORTING DEVICE FOR THE ROTATOR CUFF OF A SHOULDER JOINT OF A PERSON

[76] Inventors: Dominique Gazielly, 47 Rue Henri Dechaud, 42100 Saint Etienne; Pierre Blondel, La Forie, 63600 Ambert, both of France

[21] Appl. No.: 35,372

[22] Filed: Mar. 22, 1993

Related U.S. Application Data

[63] Continuation-in-part of Ser. No. 623,641, Dec. 13, 1990, Pat. No. 5,195,542.

[30] Foreign Application Priority Data

Apr. 27, 1989 [FR] France ............... 89 06005

[51] Int. Cl.⁶ ............................................. A61B 17/04
[52] U.S. Cl. ......................................... 606/151; 602/44; 623/19
[58] Field of Search ................... 623/1, 18, 13, 19; 602/44; 606/151; 604/180; 600/37

[56] References Cited

U.S. PATENT DOCUMENTS

| | | | |
|---|---|---|---|
| 3,029,819 | 4/1962 | Starks | 623/1 |
| 3,357,425 | 12/1967 | Morgan | 602/41 |
| 3,570,013 | 3/1971 | Blumen | 623/1 |
| 3,945,052 | 3/1976 | Liebig | 623/1 |
| 4,347,847 | 9/1982 | Usher | 606/151 |
| 4,502,161 | 3/1985 | Wall | 623/18 |
| 4,534,762 | 8/1985 | Heyer | 604/180 |
| 4,585,458 | 4/1986 | Kurland | 623/13 |
| 4,759,765 | 7/1988 | Van Kampen | 623/13 |
| 4,769,038 | 9/1988 | Bendavid et al. | 623/13 |
| 4,775,380 | 10/1988 | Seedhom et al. | 623/13 |
| 4,795,466 | 1/1989 | Stuhmer et al. | 623/13 |
| 4,932,972 | 1/1990 | Dunn et al. | 623/13 |
| 5,122,155 | 6/1992 | Eberbach | 606/151 |

FOREIGN PATENT DOCUMENTS

| | | | |
|---|---|---|---|
| 0169045 | 1/1986 | European Pat. Off. | |
| 0239775 | 10/1987 | European Pat. Off. | 606/224 |
| 358324 | 3/1990 | European Pat. Off. | 623/13 |
| 3008270 | 9/1981 | Germany | |
| 9103993 | 4/1991 | WIPO | 606/151 |

*Primary Examiner*—Gary Jackson
*Attorney, Agent, or Firm*—Parkhurst, Wendel & Rossi

[57] ABSTRACT

A rotator cuff reinforcement device adapted for surgical implantation in a shoulder of a person, comprising a strip having a base portion for fixation to a trochiter of a rotator cuff, the strip being flexible, non-tubular and flat and having at least two divergent legs extending from the base portion for fixation to at least two tendons of such a rotator cuff, the at least two divergent legs defining at least two respective divergent ends.

14 Claims, 3 Drawing Sheets

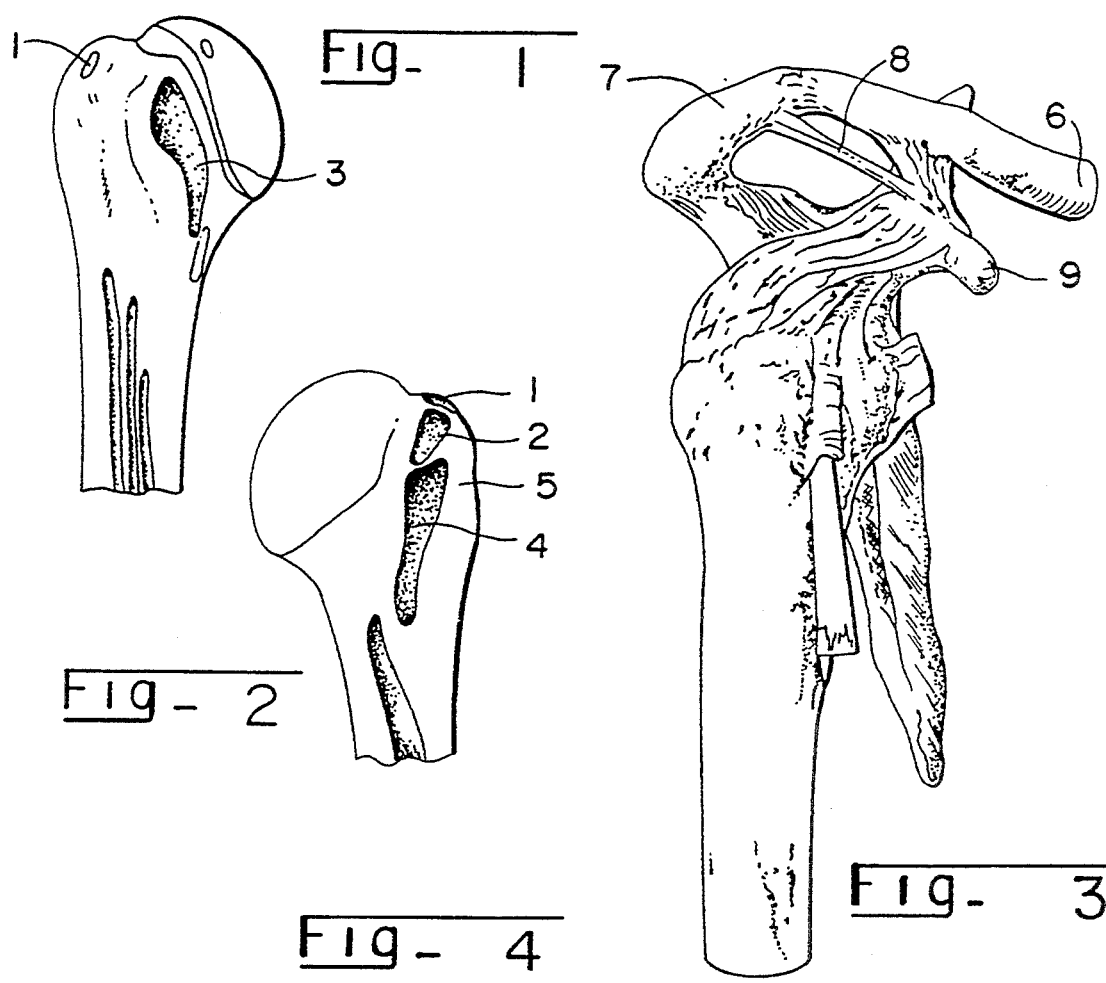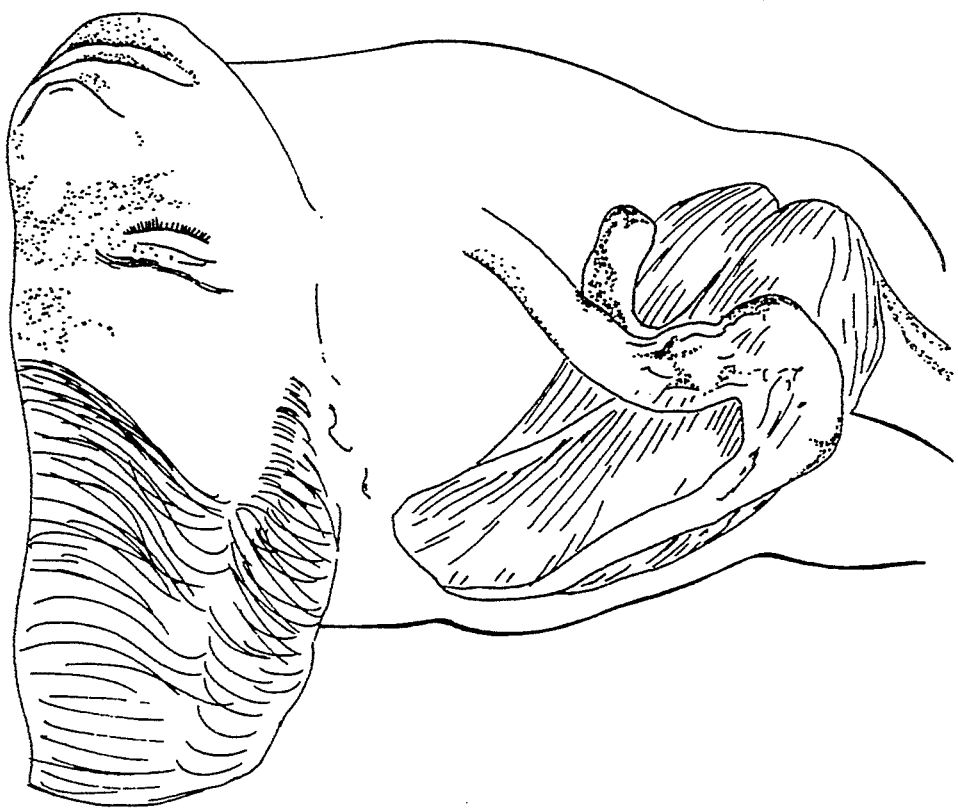

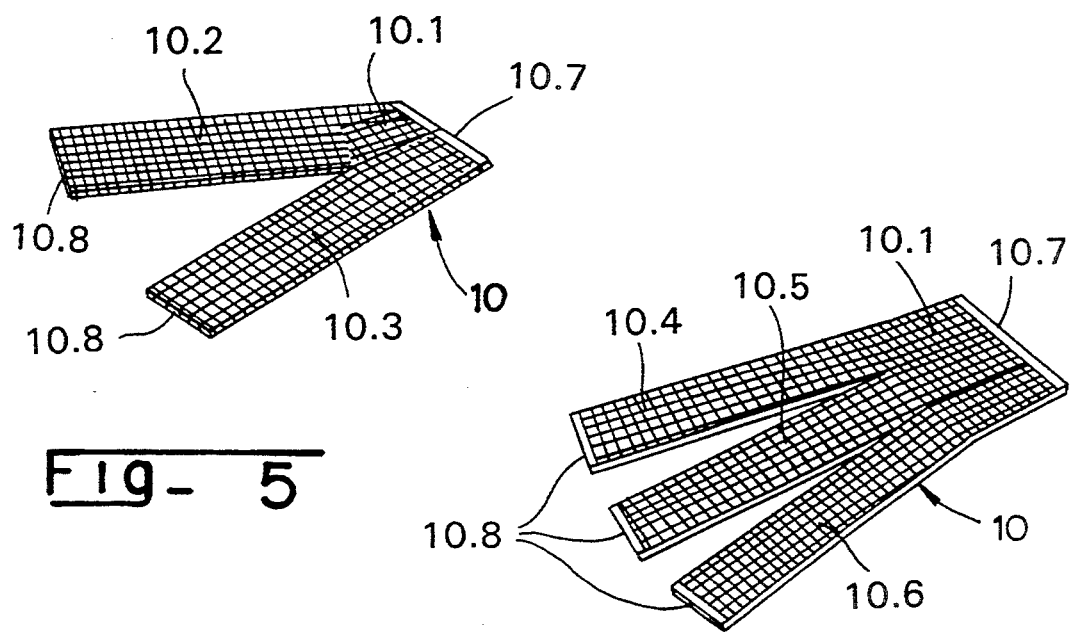
Fig. 5
Fig. 6
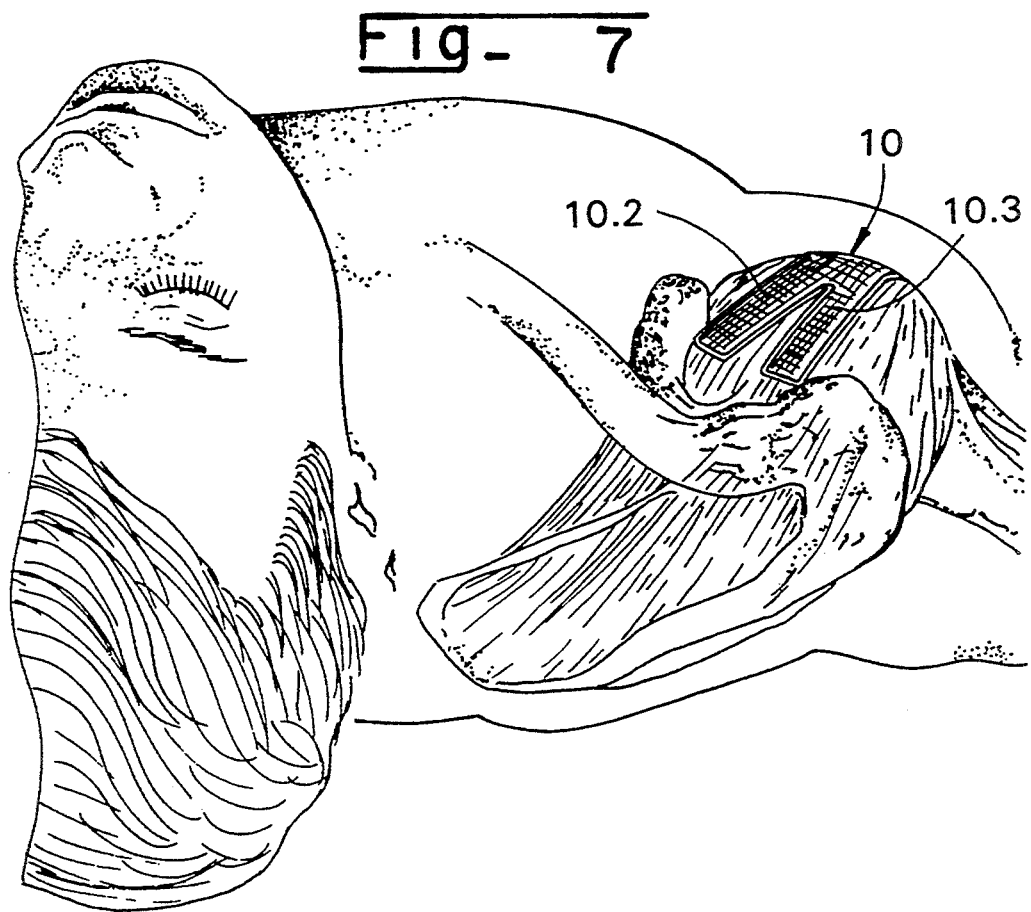
Fig. 7

REINFORCEMENT AND SUPPORTING DEVICE FOR THE ROTATOR CUFF OF A SHOULDER JOINT OF A PERSON

This is a Continuation-In-Part of application Ser. No. 07/623,641, filed Dec. 13, 1990, now U.S. Pat. No. 5,195,542.

BACKGROUND OF THE INVENTION

The invention relates to the technical sector of surgery of the shoulder and, in particular, means to provide therapy. In order to understand the objects and advantages of the invention, its environment with regard to degenerative ruptures of rotator cuffs will be briefly discussed.

Field of the Invention

As shown in the drawings, the rotator cuff or a shoulder joint is made up by a combination of the distal tendinous portion of four muscles, supraspinatus 1 and subspinatus 2, subscapularis 3 and teres minor 4, (FIGS. 1 and 2). The cuff is attached to the upper, anterior and posterior faces of the trochiter 5 by covering the upper pole of the humeral head. Proper functioning of the tendinous cuff, 3 to 4 millimeters thick, depends on the fundamental centering and stabilizing role of the humeral head with respect to sliding action during anterior and lateral lifting and rotation movements of the arm.

The musculotendinous cuff passes under an osteofibrous arch, which is made up from the front to the rear by a portion of the acromion 7, the coracoacromial ligament 8 and the coracoid process 9 (FIG. 3), thereby forming a canal. A partial section of the clavicle is shown as 6. A sliding bursa passes between the musculotendinous cuff and the walls of the osteofibrous arch. Therefore, there is a potential and sometimes detrimental interaction between the musculotendinous cuff and the acromiocoracoidian arch, particularly during lateral and anterior lifting movements of the arm. The repeated rubbing of the cuff against the walls of the osteofibrous arch results in wearing of the tendinous cuff by progressive abrasion. The rubbing can be increased in as much as arthosis lesions with severe osteophytes may thicken the walls of the aforementioned arch becoming more aggressive as the cuff gets older.

With time, gradual thinning is brought about and a trophic perforation (less than 1 cm$^2$) of the cuff, particularly in the hypo-vascularized and fragile area where the supraspinatus muscle is joined. A fall may provide a more extensive rupture by dis-junction of the supraspinatus muscle, with extension towards the front (subscapularis muscle) or the rear (subspinatus muscle). The degenerative rupture of the rotator or musculotendinous cuff may be of a varied size:
 grade 1—perforation (less than 1 cm$^2$) reaching the supraspinatus muscle;
 grade 2—supraspinatus rupture (greater than 1 cm$^2$);
 grade 3—massive rupture concerning the supraspinatus, subspinatus, subscapularis muscles and sometimes the teres minor muscle.

It is possible to carry out surgery to reconstruct the rotator cuff. This is done by re-covering the humeral head, giving back the cuff its capturing and stabilizing role and re-establishing a harmonious scapulohumeral rhythm.

Reconstruction requires excision of the coracoacromial ligament and cleaning the subacromial space, including suppression of the arthrosis legions and thinning of the anterior portion of the acromion.

Description of the Surgical Processes

Several processes are therefore possible in order to re-cover the humeral head.

Certain processes do not use the rotator cuff, such as when the tendinous cuff has disappeared due to wear or major retraction. It is technically possible to fill in the space corresponding to the cuff by covering the humeral head with a natural or synthetic, inert material. However, it appears preferable, in the case of major ruptures, where the humeral head is uncovered, to carry out plasty by the anterior deltoid muscular flap, which offers the advantage of covering the humeral head and having a lowering effect of the humeral head by active contraction of the flap.

Other surgical processes use the rotator cuff.

The rotator cuff is dis-joined. The humeral head is uncovered when there is a more or less significant lack of covering (grades 1, 2, 3). The tendons are retracted according to a variable degree, however it is possible to free the adherences in order to bring them to their initial trochiterian junction area. Just like a mobile roof, the cuff, retracted towards the scapula, covers the humeral head again. Therefore, only the tendons need to be attached to the trochiter by sutures using non-reabsorbable thread, made at the bottom of a bone trench. The reconstruction must be isometrically enabling, which may be done by visually examining, during operation, the internal and external rotation movements and the elbow against the body, and bending and extension movements, to ensure that the transosseous reinsertion sutures hold.

If the extent of the loss of tendinous substance and/or the degree of retraction prevent solid and reliable reattachment sufficient to withstand immediate and post-operative rehabilitation, it is preferable to use a deltoidian flap rather than to try to fill in the space left free by a cuff, remaining after random reattachment, by a synthetic or other type of material. In the case of average retraction which does not allow for direct reattachment of the supraspinatus muscle tendon, some recommend rotation flaps of the subscapularis muscle and/or the subspinatus muscle.

Summary of the Invention

According to the above explanations, it can be understood that surgery of the shoulder is delicate, complex and a maximum of precautions have to be taken in order to guarantee the operation reliable. It is also necessary to take into account the fact that the tissues are worn, thin and old. It is for this reason that a first aim according to the present invention was to look into reinforcing the reattached tendons which are thin or fragile (including by infiltrations of corticoids) and thus to provide surgical therapy for the rupture or weakening of the rotator cuff of a shoulder joint of a person. Another aim according to the invention was to produce a simple device, easily manufactured and biologically compatible within the human body. Another aim according to the invention was to provide mechanical reinforcement by adding a substance enabling the tendinous reattachment zone to be protected and facilitating more active post-operative rehabilitation.

Another aim according to the invention was to obtain thickening of the tendons, enabling a final biological reinforcing effect by integration of the material initially added.

These aims and others shall be made well apparent from the following description.

According to a first characteristic, the device used for aiding in surgical therapy of the rupture or weakening of the rotator cuff of a shoulder joint of a person, is characterized by a thin, non-tubular strip having a base portion to be fixed onto the trochiter. At least two divergent legs extend toward the top of the cuff and having end(s) thereof to be fixed onto the tendon(s). One of the legs is fixed to the repaired tendon in order to reinforce it and protect it and the other leg(s) are fixed onto the other healthy tendon(s) according to the biomechanical working axes of the shoulder rotator cuff tendons. The base portion is inserted into a trench or groove formed in the trochiter and sutured therein.

BRIEF DESCRIPTION OF THE DRAWINGS

In order to clarify the invention, in a non-limiting manner, the invention is illustrated by the accompanying drawings wherein:

FIGS. 1 and 2 are partial views of the anterior and posterior face of the top end of the right humerus of the person.

FIG. 3 is an external side view of the joints of the right shoulder.

FIG. 4. is a top view showing the rotator cuff.

FIG. 5 is view of a tendon holding and supporting device according to the present invention comprising a base portion extended by two legs.

FIG. 6 is a view of the device as an alternative model comprising a base portion and three legs.

FIG. 7 is a view illustrating the application of the device according to the invention in order to support certain tendons.

Figure 8:
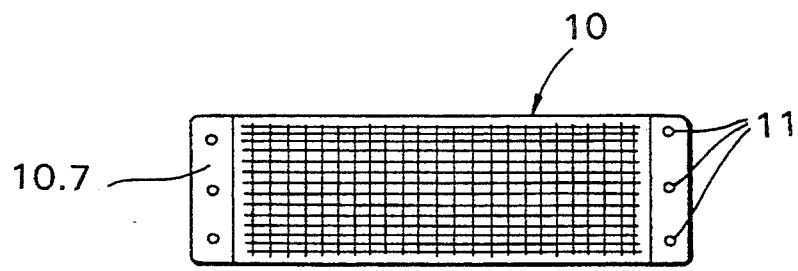
FIG. 8 shows the device seen in a plan view, in a simple geometrical form.
Figure 9:
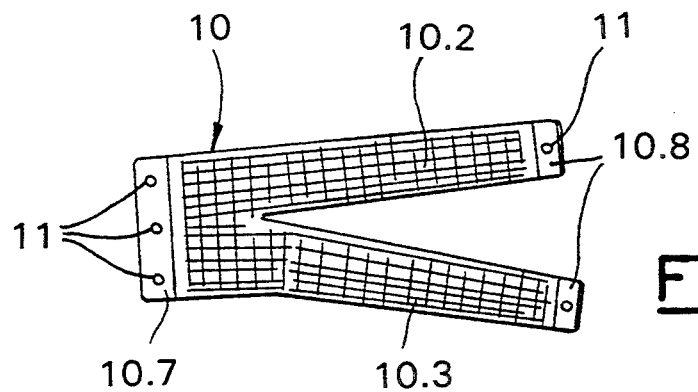
FIGS. 9 and 10 are views showing the device of FIGS. 5 and 6 provided with fixing means at its ends.
Figure 10:
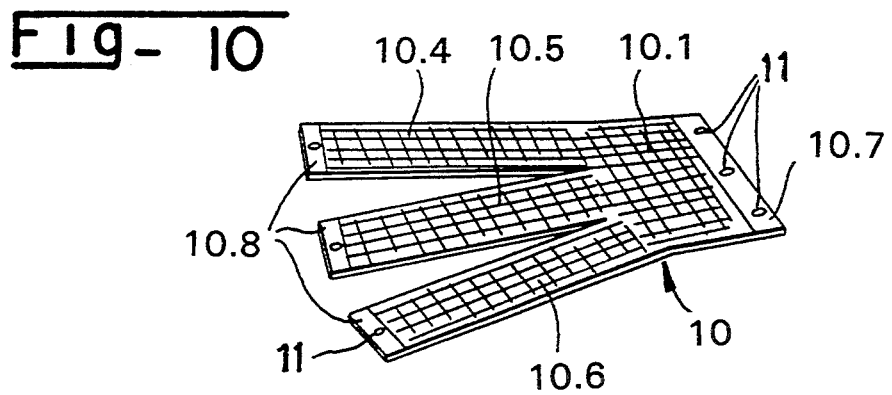

The objects of the invention will become more apparent from the following non-limiting detailed description, when considered in conjunction with the drawings.

DETAILED DESCRIPTION OF THE PREFERRED EMBODIMENTS

The device according to the present invention is used in surgical therapy of the rupture or weakening of the rotator cuff of a shoulder joint.

The device is in the form of a strip 10 having two or three legs (10.2, 10.3, 10.4, 10.5, 10.6). The device is produced in the form of a strip by, for example, braiding, knitting or weaving a biocompatible material. The strip is thin, sterile, biocompatible and short. The strip has, firstly, a base portion 10.1 fixed by its ends 10.7 on the trochiterian support, and, secondly, has two or three legs diverging towards the top of the cuff according to the biomechanical working axes of the rotator cuff tendons.

The number and count of the thread used for making the reinforcement device is of a type to provide maximum tensile strength with a minimum of thickness (e.g., polypropylene). The total thickness is less than or equal to 1 mm so as to avoid any risk of interference. The reinforcement device has high flexibility, optimum covering power for satisfactory isometry (to maximize spreading of the braid and legs), and satisfactory resistance to side sutures. Further, the present reinforcing device may be rapidly integrated by living tissues. The width of the base portion may be within a range of 14 to 26 mm, and the width of the legs is about one-third to one-half that of the base portion. Preferably the width of the base portion is 20 mm, and that of the legs is 8 mm. The total length is adapted to the morphology of the patient, and is at least 20 mm, and preferably, within a range of about 40 to 65 mm. The ends may be heat-sealed so as to form a semi-rigid solid mass. Polypropylene thread (1100 DTEX) having a number of threads of $32 \times 2$ threads may be utilized. Preferably, the strip has a mesh size of about 8 meshes per an inch. The end of the base portion may be sealed along a width of 5 mm, and the ends of the legs may be sealed along a width of 3 to 4 mm.

The strip is extended towards the front by at least two divergent legs 10.2 and 10.3 defining a Y shape, for application and fixing to tendons (FIG. 5). In an alternative form, according to FIG. 6, the strip has three diverging legs 10.4, 10.5 and 10.6. The general aspect of the strip as such, is rectangular or trapezoidal shaped and enables the reinforced cuff to work according to the biomechanical lines of forces, in the direction of the different tendons. According to a specific positioning, one of the legs 10.2 and 10.3, or 10.4, 10.5 and 10.6, is fixed an sewn by the end 10.8 onto the repaired tendon, thinned down and thus reinforced thereby protecting it, whereas the other leg(s) of the strip are sewn to the ends 10.8 on the other healthy tendon(s). The shape of the strip with three legs thereby enables sewing onto the supraspinatus, subspinatus and subscapularis tendons.

The legs 10.2, 10.3, 10.4, 10.5 and 10.6 can be the same length or different lengths.

In its linear shape, the strip provides support of the tendon during weakening before rupture.

According to another arrangement, the ends 10.7 and 10.8 are made up of a semi-rigid or flexible mass resulting from melting the component treads. The ends may include holes 11, facilitating the binding of the device on the trochiter and on the healthy tendon(s). These holes exist in a number adapted to provide binding and fixing.

Therefore, the shape of the holding and supporting device according to the invention enables it to match the tendons of the rotator cuff perfectly thereby taking up a minimum of space so as not to cause an iatrogenic subacromial anterior conflict by increasing the bulk of the rotator cuff.

Furthermore, the device must be positioned on a reconstructed cuff, in an isometric manner, in order to enable the tendons to operate in the direction of the fibers and without excessive pulling.

According to another arrangement of the invention, the holding and supporting strip is made of a biologically compatible material, thus enabling it to be biologically integrated into living tissues. In an advantageous manner, this is a braided polypropylene material. The material selected, enables gradual integration of the reinforcing and holding strip thereby providing thickening of the reconstructed cuff and therefore, biological reinforcement.

The advantages are clearly set forth in the present specification. In particular, the simplicity of the design of the reinforcing and holding strip, its easy adaptation to a reconstructed, re-joined cuff, are highlighted.

What is claimed:

1. A rotator cuff reinforcement device adapted for surgical implantation in a shoulder of a person, comprising:

a strip consisting of a single layer of braided polypropylene material having a base portion for fixation to a trochiter and at least two divergent legs extending from said base portion for fixation to at least two tendons of such a rotator cuff, said at least two divergent legs defining at least two respective divergent ends, said strip being flexible, non-tubular and flat, wherein said base portion and said at least two divergent legs are substantially planar and extend along the substantially same plane, and two of said at least two divergent legs diverge from each other by an angle in said plane.

2. The device of claim 1, wherein a thickness of said strip is not greater than about 1 mm.

3. The device of claim 1, wherein a length of said strip is within a range of about 40 to 65 mm.

4. The device of claim 1, wherein a width of the base portion of said strip is within a range of about 14 to 26 mm.

5. The device of claim 4, wherein the width of said strip is about 20 mm.

6. The device of claim 1, wherein a width of the divergent legs of said strip is within a range of about 5 to 13 mm.

7. The device of claim 6, wherein the width of the divergent legs of said strip is about 8 mm.

8. The device of claim 1, wherein a width of the legs is about one-third to about one-half a width of the base.

9. The device of claim 1, wherein said strip comprises two divergent legs.

10. The device of claim 1, wherein said strip comprises three divergent legs.

11. The device of claim 1, wherein said strip is biocompatible.

12. The device of claim 1, wherein said strip is trapezoidal.

13. The device of claim 1, wherein said strip is sterile.

14. The device of claim 1, wherein each of the ends of the strip comprises a semi-rigid mass resulting from melting a portion of the braided polypropylene, said masses including holes for facilitating binding of the device to a trochiter and to tendons.

* * * * *